(12) United States Patent
Herendeen et al.

(10) Patent No.: US 8,189,189 B1
(45) Date of Patent: May 29, 2012

(54) LED SENSOR FOR PROCESS CONTROL

(76) Inventors: Robert O. Herendeen, San Jose, CA (US); James L. Beck, Los Gatos, CA (US); Larry Perazzo, San Jose, CA (US)

( * ) Notice: Subject to any disclaimer, the term of this patent is extended or adjusted under 35 U.S.C. 154(b) by 420 days.

(21) Appl. No.: 12/576,138

(22) Filed: Oct. 8, 2009

Related U.S. Application Data

(60) Provisional application No. 61/103,674, filed on Oct. 8, 2008.

(51) Int. Cl.
*G01J 3/44* (2006.01)
(52) U.S. Cl. .................................... 356/300; 356/301
(58) Field of Classification Search ............... 356/300, 356/301
See application file for complete search history.

(56) References Cited

U.S. PATENT DOCUMENTS

| | | | |
|---|---|---|---|
| 4,938,602 A * | 7/1990 | May et al. ................ | 356/435 |
| 5,362,652 A * | 11/1994 | McClain .................. | 436/135 |
| 5,585,626 A | 12/1996 | Beck | |
| 5,638,172 A * | 6/1997 | Alsmeyer et al. ........ | 356/301 |
| 5,763,873 A | 6/1998 | Beck | |
| 5,789,741 A | 8/1998 | Kinter | |
| 5,793,035 A | 8/1998 | Beck | |
| 5,809,440 A | 9/1998 | Beck | |
| 5,837,997 A | 11/1998 | Beck | |
| 6,011,882 A | 1/2000 | Dasgupta | |
| 6,122,042 A | 9/2000 | Wunderman | |
| 6,208,749 B1 | 3/2001 | Gutkowicz-Krusin | |
| 6,560,038 B1 | 5/2003 | Parkyn, Jr. | |
| 6,880,954 B2 | 4/2005 | Ollett | |
| 7,139,076 B1 | 11/2006 | Marbach | |
| 7,189,983 B2 | 3/2007 | Aguirre | |
| 7,250,611 B2 | 7/2007 | Aguirre | |
| 7,329,887 B2 | 2/2008 | Henson | |
| 7,401,943 B2 | 7/2008 | Okamitsu | |
| 2002/0128398 A1 * | 9/2002 | Dessipri et al. .......... | 250/339.01 |
| 2003/0032366 A1 | 2/2003 | Cerni | |
| 2003/0038112 A1 | 2/2003 | Liu | |
| 2003/0119199 A1 * | 6/2003 | Wolf et al. ............... | 436/164 |
| 2005/0158864 A1 * | 7/2005 | Brant et al. .............. | 436/37 |
| 2006/0044555 A1 * | 3/2006 | Wang et al. .............. | 356/301 |
| 2007/0030488 A1 | 2/2007 | Harrison | |
| 2007/0216069 A1 * | 9/2007 | Imai et al. ............... | 264/408 |
| 2008/0183312 A1 | 7/2008 | Funk | |
| 2008/0305459 A1 * | 12/2008 | Li et al. ................... | 433/226 |

OTHER PUBLICATIONS

U.S. Appl. No. 12/390,384, filed Feb. 20, 2009, Perazzo, Larry.
U.S. Appl. No. 12/538,060, filed Aug. 7, 2009, Beck, James L.
U.S. Appl. No. 12/431,728, filed Apr. 28, 2009, Orner, William.
Luxeon Dental: Technical Data DS35. Philips LumiLeds Document #DS35 [online], Feb 12, 2004 [retrieved on Sep. 29, 2009]. Retrieved from the Internet: <URL: www.philipslumileds.com/pdfs/ds35.pdf>.

* cited by examiner

*Primary Examiner* — Kara E Geisel
(74) *Attorney, Agent, or Firm* — Fernandez & Associates, LLP

(57) ABSTRACT

The invention relates to a device and method for monitoring a chemical reaction proceeding from a first state to a second state by emitting and detecting radiation in ranges of interest for a spectral signature of the material undergoing the chemical reaction. Using the concept of optical spectral detection and identification, it is therefore possible to utilize a combination of specific emitters and detectors, optics and signal processing in order to identify materials and events.

29 Claims, 18 Drawing Sheets

Reflective Mode

Transmission Mode

Optical Head
for Reflective Mode

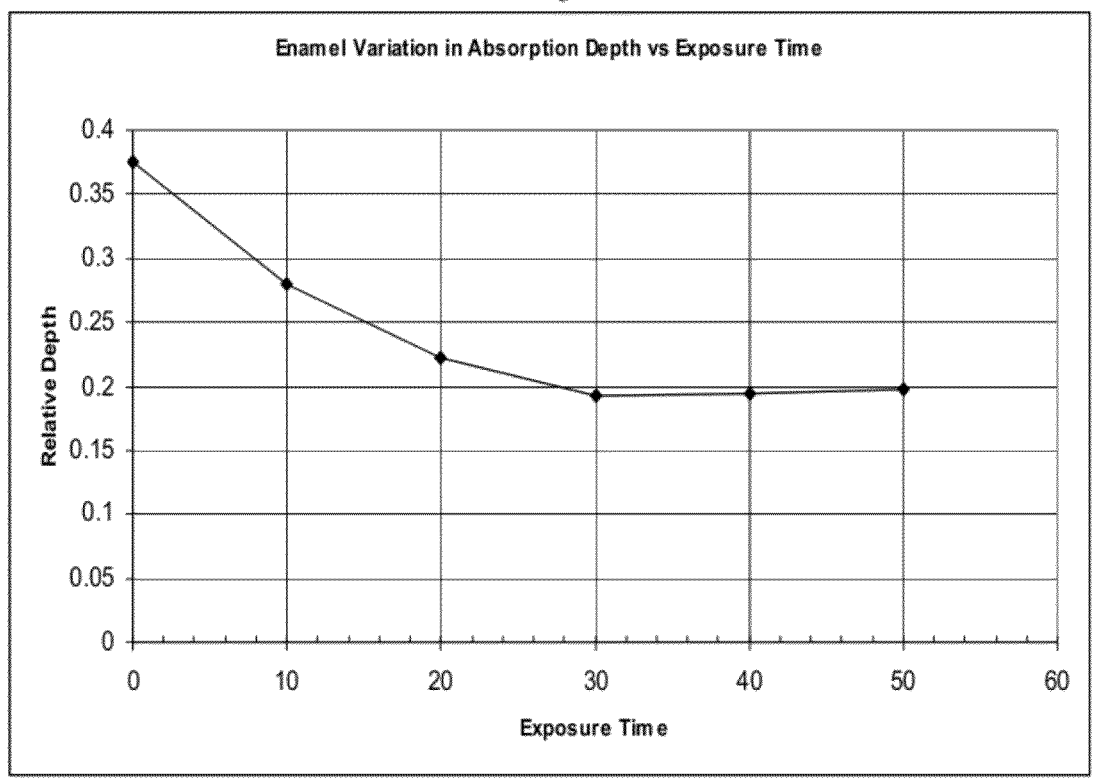

Definition:
Depth of Absorption Band = Y4 - Y1

LED SENSOR FOR PROCESS CONTROL

PRIORITY

This application claims priority from U.S. 61/103,674 filed on Oct. 8, 2008, included herein in its entirety by reference.

CROSS REFERENCE TO RELATED APPLICATIONS

The following patents and applications bear on the instant invention and are included herein in their entirety by reference; U.S. Pat. No. 5,585,626, U.S. Pat. No. 5,763,873, U.S. Pat. No. 5,789,741, U.S. Pat. No. 5,793,035, U.S. Pat. No. 5,809,440, U.S. Pat. No. 5,837,997, U.S. Pat. No. 6,560,038, U.S. Pat. No. 6,880,954, U.S. Pat. No. 7,189,983, U.S. Pat. No. 7,250,611, U.S. Pat. No. 7,329,887, U.S. Pat. No. 7,401,943, U.S. Pat. No. 7,139,076, U.S. Pat. No. 6,122,042, U.S. Pat. No. 6,016,372, U.S. Pat. No. 6,011,882, U.S. 2007/0030488, U.S. 2008/0183312, U.S. 2003/0038112, U.S. 2003/0032366 and applications owned by the same Assignee, U.S. Ser. No. 12/390,384; U.S. Ser. No. 12/538,060; U.S. Ser. No. 12/431,728.

BACKGROUND OF THE INVENTION

1. Field of the Invention

The invention relates to a device and method for monitoring a chemical reaction proceeding from a first state to a second state by emitting and detecting radiation, reflected or transmitted, at points of interest for a spectral signature of the material undergoing the chemical reaction.

2. Prior Art

Optical technology using a combination of solid state emitters and detectors has been in use for over 20 years to measure and detect materials and events, such as blood oximetry, blood glucose levels, bacterial levels, the presence of certain types of cancer, paint color, fluid transmission in delivery tubes, paint colors, weed discrimination in agriculture, dye purities and for various food processing quality control.

The fundamental technology used in most of these applications is spectroradiometry, whereby mostly visible and specific wavelengths are detected by reflection or transmission into a detector from a suitable emitter, and the resultant signal levels used in an algorithm to provide a suitable control output from the measurement system. For example, water and $CO_2$ have absorption lines at 2002 and 2004 nm. Conventional spectroradiometers are designed to measure the spectral power distribution of various illuminants. Spectral signatures are specific combinations of reflected and/or transmitted and absorbed electromagnetic radiation at varying wavelengths which can uniquely identify an object. The spectral signature of an object is a function of incident electromagnetic radiation wavelength(s) and the object's material interaction with those section(s) of the spectrum. A material's black body radiation emission, surface finish and other factors all interact to produce a spectral signature. Measurements can be made with various instruments, including a task specific spectrometer or detectors sensitive to specific regions of interest.

In an example of oximetry, or the measurement of the percentage of oxygenated hemoglobin, the calculation is done in a system that calculates the ratio of oxygenated hemoglobin to total hemoglobin by reflective or transmissive spectral response at two distinct wavelengths, typically 660 nm and 940 nm. Because the spectral characteristics differ at those wavelengths, then a quantitative series of measurements can be made during the arterial pulse and using a well defined algorithm, the output can be calculated and displayed. The system that makes this measurement must deal with establishing the location of the arterial pulse, sampling multiple times during the pulse, dealing with noise issues caused by movement and ambient light and finally calculating the value and providing a digital readout. A byproduct is also the pulse rate. See the sample spectral curves in FIG. 5 for Hb and $HbO_2$.

With the advent of more light sources and more sophisticated detection methods, it is possible to detect spectral characteristics outside of the visible range that can be used to identify even more materials and events, both organic and inorganic. When chemical reactions take place a spectral signature of the constituents may produce additional and repeatable new characteristics, either in the form of absorption or reflection characteristics or the shape of the spectral curves. In this case it is therefore possible to detect not only the fundamental materials but also the resultant reaction. It is important to note that the added factor of curve shape has been added to optical spectroscopy, which can be used to enhance the identification process. The spectral signature in this case is determined through the use of one or more light emitters and one or more suitable detectors in order to determine the spectral response. A change in a spectral signature therefore makes it possible to identify any of the resultant constituents. It is also possible to add fluorescent markers to the constituents in order to enhance the spectral effects, both inside and outside the visible spectrum, such as might be used with cell identification by adding photo sensitive proteins that attach themselves to the cell structure, or by adding certain fluorescent additives to organic reactions that appear or disappear as a result of the reaction. Another example is that it has been demonstrated that resin double bonds in acrylic materials disappear during the curing process, resulting in the reduction or elimination of an absorption band in the neighborhood of 1.6μ.

BRIEF DESCRIPTION OF THE INVENTION

Using the concept of optical spectral detection and identification, it is therefore possible to utilize a combination of specific emitters and detectors, optics and signal processing in order to identify materials and events. Using the example of the reaction signature of acrylic materials as used in modern dentistry, it is possible to detect the presence or absence of the 1.6μ absorption band and determine the degree of cure. These materials are typically cured using wavelengths of blue light around 465 nm from a solid state light source, through an optical wand. By integrating additional optics, emitters and detectors and a signal processing system, it is possible to detect the completion of cure and produce a control signal for stopping the curing process by terminating the "curing wavelength(s)". The instant invention results in tighter control over the degree of cure and reduces the uncertainty in proper cure times and minimizes the actual radiation time to achieve a given cure.

In similar organic reaction processes with multiple absorption bands, even if the absorption does not completely disappear, or if new reflectance or absorption bands are created, then the relationship or ratio of these specific bands can be used to identify reactive components, along with spectral slope measurements, all of which comprise input to a process control algorithm to monitor and control more complex systems, reactions and impurities. Such a system can be used to identify fluids in tube delivery systems as found in medical and chemical processes. The instant invention discloses an optical module that provides a suitable window for reflective and/or transmissive spectral measurements, coupled with a signal processing system. Since the specific optical characteristics are related to molecular and atomic configurations, then the bandwidths are more narrow than photosensitive dye processes and therefore a more accurate identification can take place. In a situation where spectroradiometry is used for identification, moving the identification process to a more narrow and material specific spectral signature, improves the accuracy of the process.

The instant invention is concerned with chemical reactions wherein an initial composition of matter undergoes a transformation from one state to another. For purposes of the instant invention materials of interest are those wherein a change in reflectance and/or transmittance occurs as a reaction is taking place within a given material across a narrow spectral range characterized by a minimum number of discrete wavelengths; in some embodiments this number is five or less discrete wavelengths. An exemplary reaction is polymerization wherein some chemical bonds may be formed and some may be broken; other reactions included herein involve different compounds brought together and a reaction initiated by heat or some other initiator or stimulus such that the compounds react and form a different compound(s). A goal of the instant invention is to monitor the progress of the transformation optically by sensing changes in one or more regions of a spectral signature based upon a change in reflectance or transmission or a combination of both. As shown in FIG. 3, a change may be one of relative signal amplitude across a band 310, slope change across a band 320, or adsorption peak change across a very narrow band 330; other changes in a spectral signature may be used, as appropriate. Critical characteristics of useful spectral changes are that the changes are repeatable and indicative of the progress of a chemical reaction from initiation to completion. In some embodiments reference data is known for a given material and how its spectral signature changes over time versus degree of completion and/or stimulus provided. In some embodiments adsorption and/or transmission decreases upon curing or reaction; in some embodiments adsorption and/or transmission in a spectral region increases while decreasing in another region.

DETAILED DESCRIPTION OF THE INVENTION

In some embodiments a spectral identification and/or monitoring system comprises the following components:
1. One or more emitters and one or more detectors, suitable for the spectral regions of interest. In some embodiments an emitter may not be required when the object of interest is emitting itself or other radiation is present.
2. An emitter drive and control system, including any modulation circuitry required.
3. Detector system with suitable amplification, demodulation, noise processing and data processing with a suitable output for data and logical control of any peripheral systems.
4. A power supply with compatible system control and regulation.
5. Suitable optical components for the direction and control of both energy from the emitter and resultant or reflected energy from a material under test, back to the detector.
6. Suitable packaging for thermal management and control.
7. In some embodiments an emitter is a LED or a solid state laser emitting at a specific wavelength, $\lambda_0$, within a wavelength range of about ±3 nm. In some embodiments an emitter is two or more LEDs or lasers emitting at wavelengths, $\lambda_1, \lambda_2, \lambda_3 \ldots \lambda_n$, each within a wavelength range of about ±3 nm about a predetermined wavelength; typically n is $\leq 5$.

Figure 1:
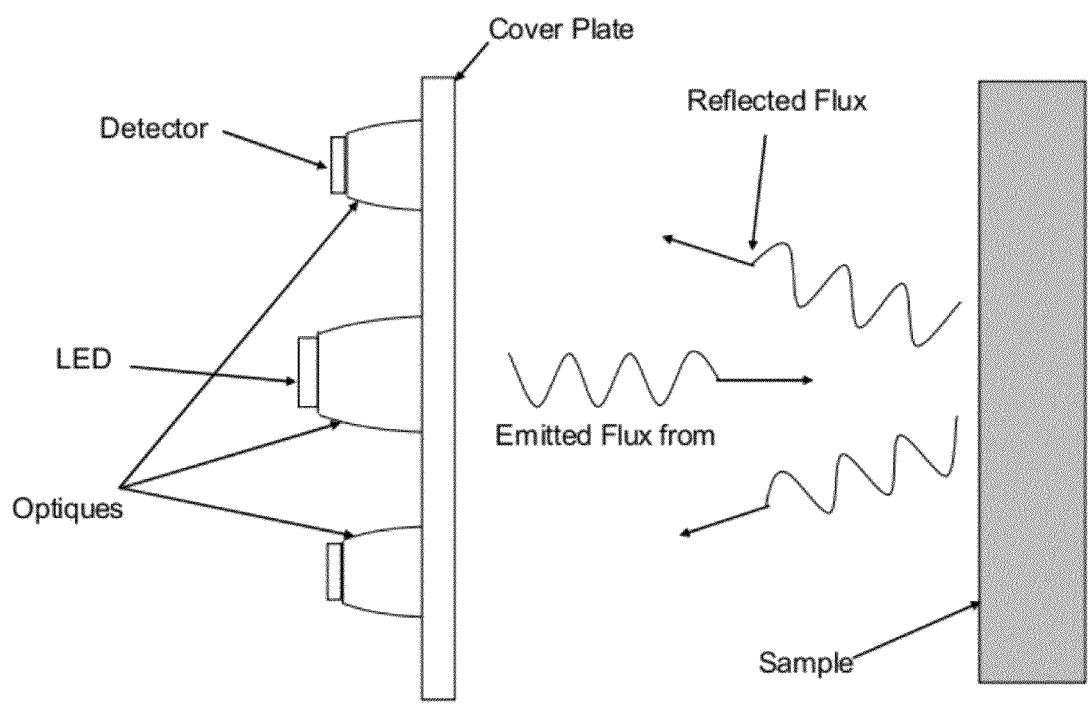
FIG. 1 is a sketch of one embodiment for reflectance.
Figure 2:
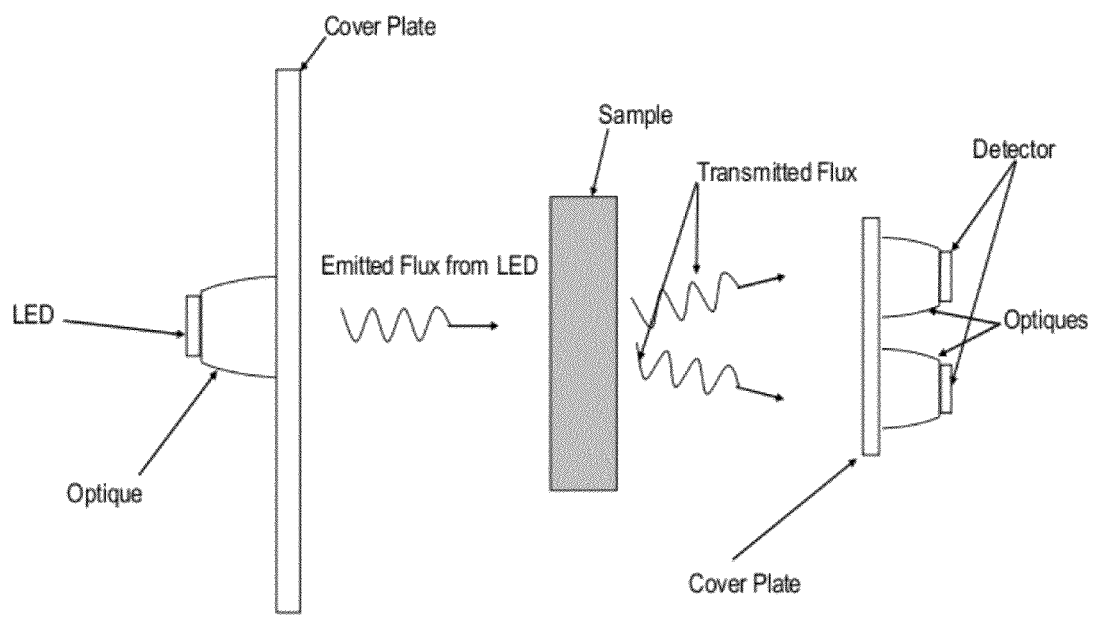
FIG. 2 is a sketch of one embodiment for transmission.

An illustrative example of a system capable of employing the techniques previously discussed is illustrated as in FIGS. 1 and 2. A LED is functioning as an emitter; detectors and emitters/LEDs have optional optiques around them to improve emission and capture efficiencies.

In some embodiments a spectral identification and/or monitoring system comprises one or more light sources and one or more light detectors. "Light" in this context includes electromagnetic radiation from sub-x-ray to far IR portions of the spectrum. Light sources, or emitters, comprise LEDs, lasers, incandescent bulbs, halogen bulbs, fluorescent bulbs or any other suitable radiation source having adequate spectral content at required wavelengths.

In some embodiments a spectral identification and/or monitoring system comprises one or more radiation detectors, including silicon photodetectors and other photodetectors having adequate response at appropriate wavelengths. The following is a partial list of typical detectors used for various wavelength bands:

| Detector Type: | Wavelength Range (μm) |
| --- | --- |
| Germanium, Avalanche | 0.8-1.8 |
| Germanium, Photoconductive | 0.5-1.8 |
| Germanium, PIN | 0.5-1.8 |
| Germanium, Photon Drag | 9-11 |
| Germanium, Gallium-doped | 60-120 |
| Indium Antimonide | 1-5.5 |
| Indium Arsenide | 1-3.8 |
| Indium Gallium Arsenide, Avalanche | 0.9-1.7 |
| Indium Gallium Arsenide, PIN | 1-1.7 |
| Indium Gallium Arsenide, Phosphide | 0.9-1.65 |
| Lead Selenide, Ambient | 1-4.8 |
| Lead Selenide, TE-cool\ld | 1-5.5 |
| Lead Selenide, LN2-cooled | 1-6.8 |
| Lead Sulfide, Ambient | 1-3 |
| Lead Sulfide, TE-cooled | 1-3.3 |
| Lead Sulfide, LN2-cooled | 1-4 |
| Mercury Cadmium Telluride, Photoconductive | 2-20 |
| Mercury Cadmium Telluride, Photoelectromagnetic | 3-12 |
| Mercury Cadmium Telluride, Photovoltaic | 8-12 |
| Silicon, Avalanche | 0.4-1.1 |
| Silicon, Photoconductive | 0.18-1.15 |
| Silicon, Photovoltaic | 0.18-1.15 |
| Silicon, PIN | 0.2-1.2 |
| Silicon, Gallium-doped | 8-17 |
| x-ray detector | <.050 |
| alpha particle detector | <.025 |
| gamma particle detector | <.010 |

Light sources and light detectors are matched in such a way that a response to signals from any single light source can be isolated and discriminated from similar stimulation from other light sources. Light sources to be discriminated from each other can be sources within the system or sources outside the system, such as ambient lighting, solar radiation or other sources of radiation within the spectral bandwidth of a system. Methods for matching light sources to light detectors include filtered light sources, filtered light detectors or various modulation schemes that allow a detector to be selective of which light source it "sees" or receives at any given point in time. Such modulation schemes include synchronous emitter/detector pairs, where a form of time-division multiplexing is used to isolate the various signals. Other modulation schemes can involve frequency or phase modulation to isolate the detected signals. Still other modulation schemes might include digital coding algorithms such as those used in voice and data communications.

LEDs and one or more detectors to assess differences in a generalized test material prior to, during and subsequent to some form of a processing event are disclosed. A system may be used in either reflective or transmission mode or a combination mode; note FIGS. 1 and 2. LED(s) irradiate a test sample and reflected or transmitted radiant flux is sensed by detectors, optionally, some detectors are filtered; some detectors comprise optional optiques.

Figure 3:
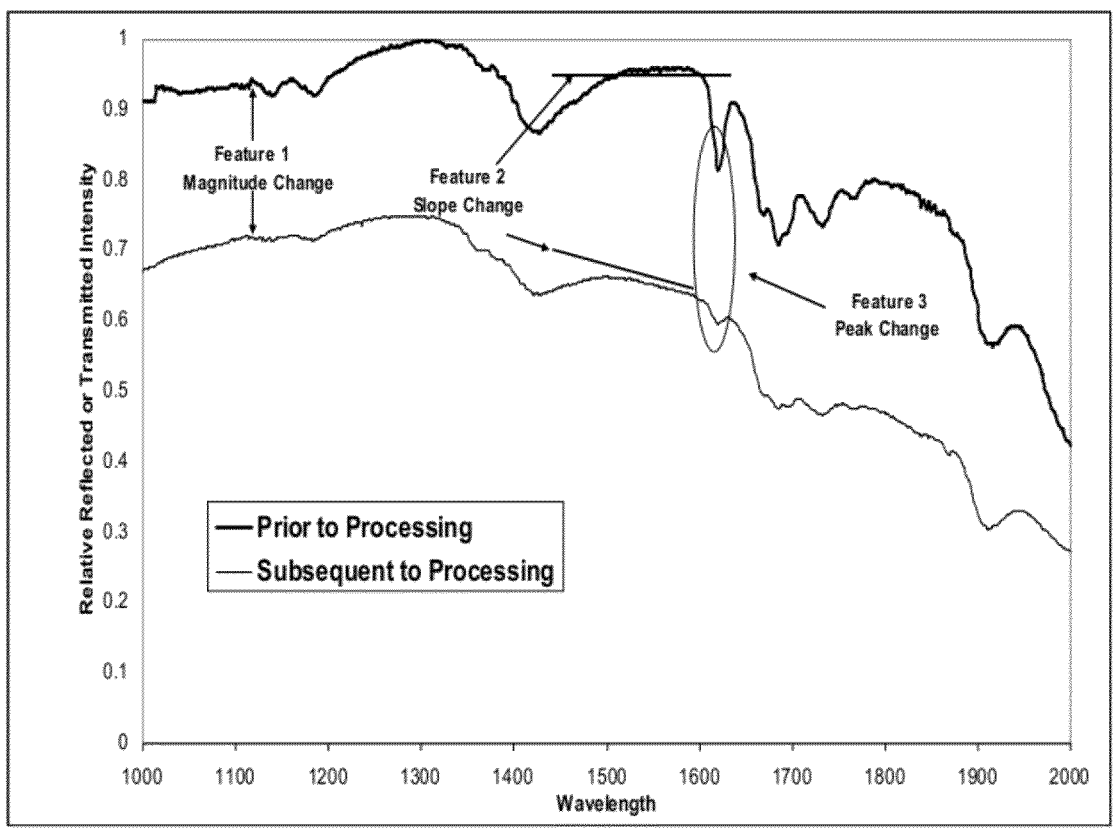
FIG. 3 is an exemplary spectral signature of a material.

FIG. 3 presents an arbitrary spectral power reflectance or transmission plot illustrating the different features that the invention is capable of assessing. Feature 1 represents a straightforward drop in reflected or transmitted radiant flux after processing. Feature 2 illustrates a change in the slope before and after processing over a specific wavelength range. Feature 3 illustrates a change in the strength of a reflected or transmitted absorption band. Additionally the number of detectors can be increased and positioned such that the invention can measure changes in polarization, bidirectional reflectance distribution function (BRDF), bidirectional transmission distribution function (BTDF) as well Raman and Rayleigh scattering and other features known to one knowledgeable in the art; in some embodiments Fourier transforms of the spectral data may be done.

Figure 4:
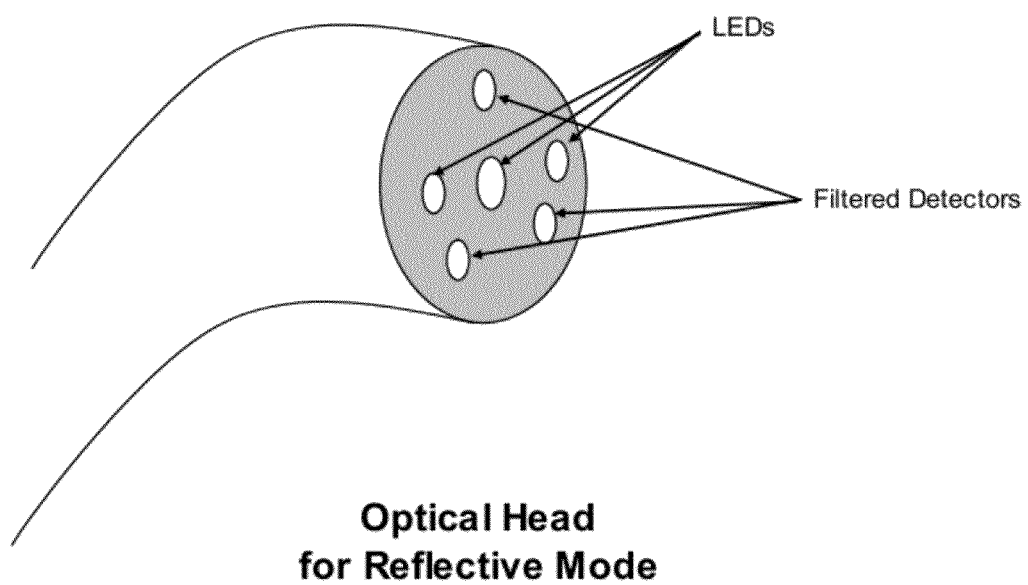
FIG. 4 is a sketch of an optical head of one embodiment.
Figure 5:
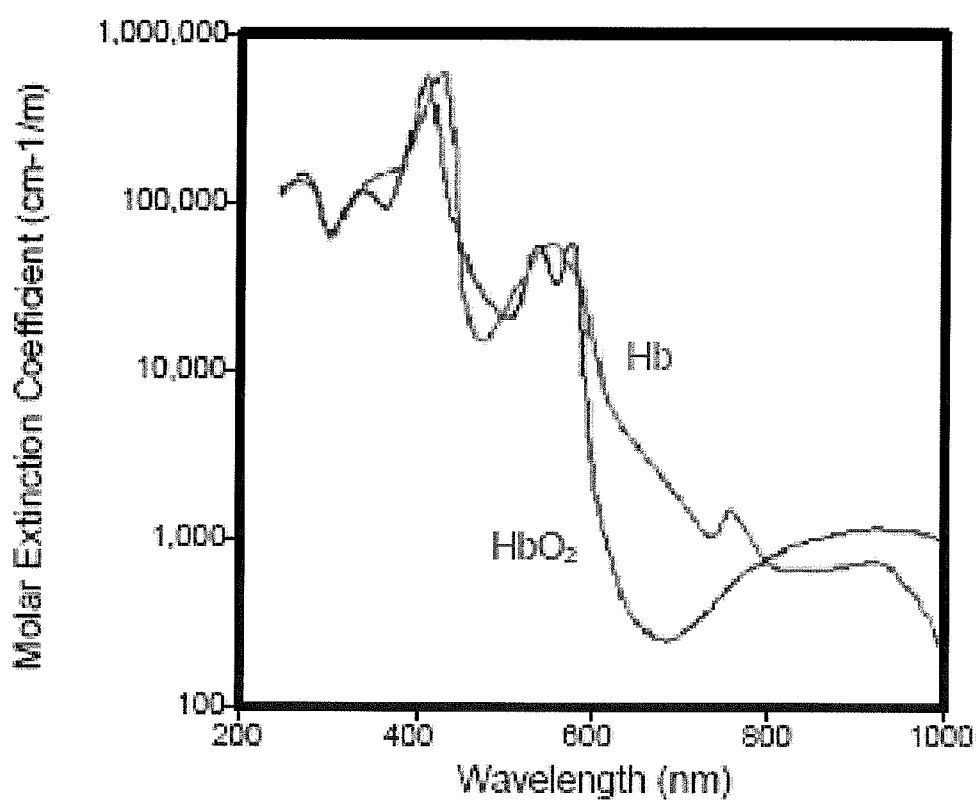
FIG. 5 is a scan of $HbO_2$ and Hb from subcutaneous blood.
Figure 6:
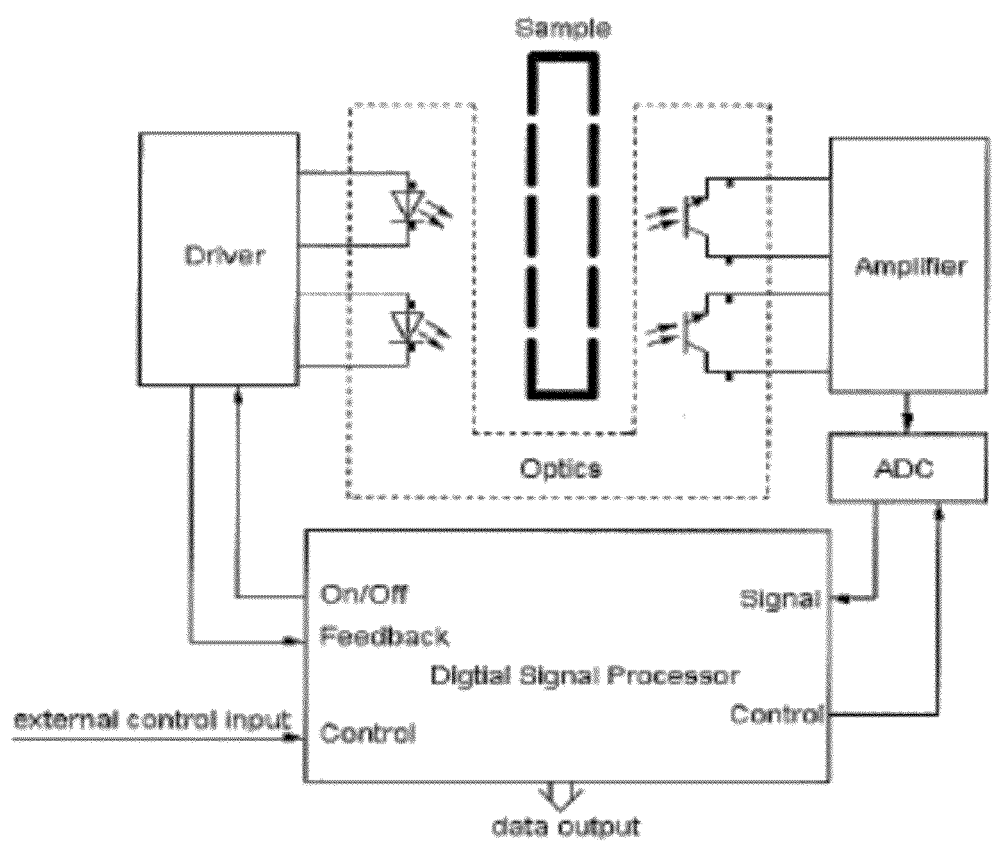
FIG. 6 is a block diagram of one embodiment.
Figure 7A:
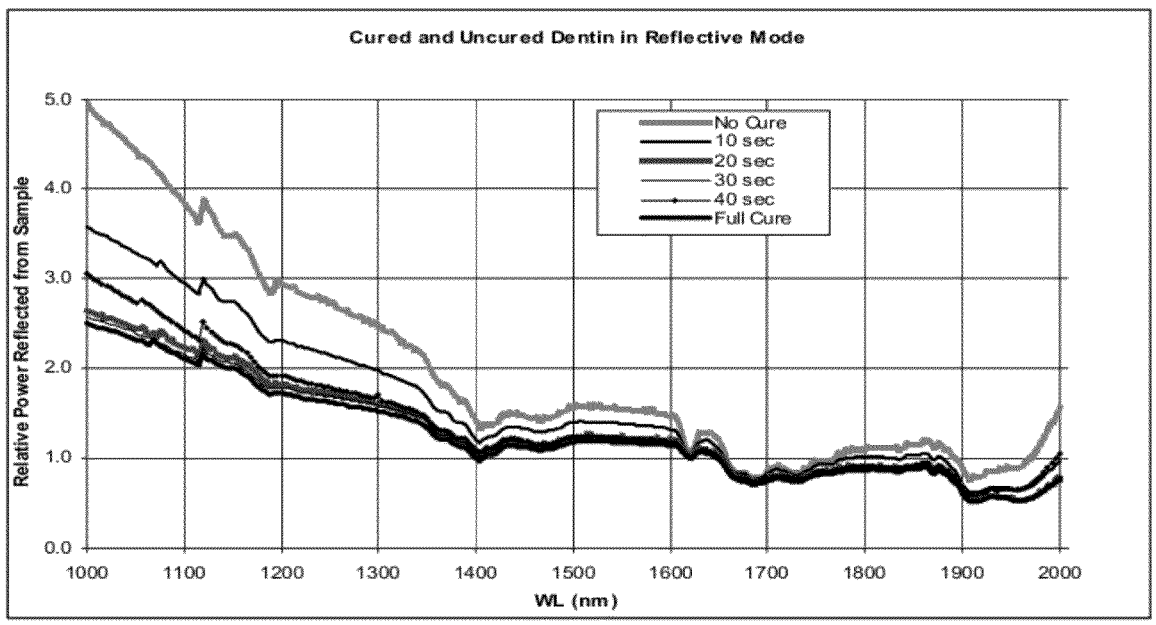
FIG. 7A, B, C exemplary curves of Dentin.
Figure 7B:
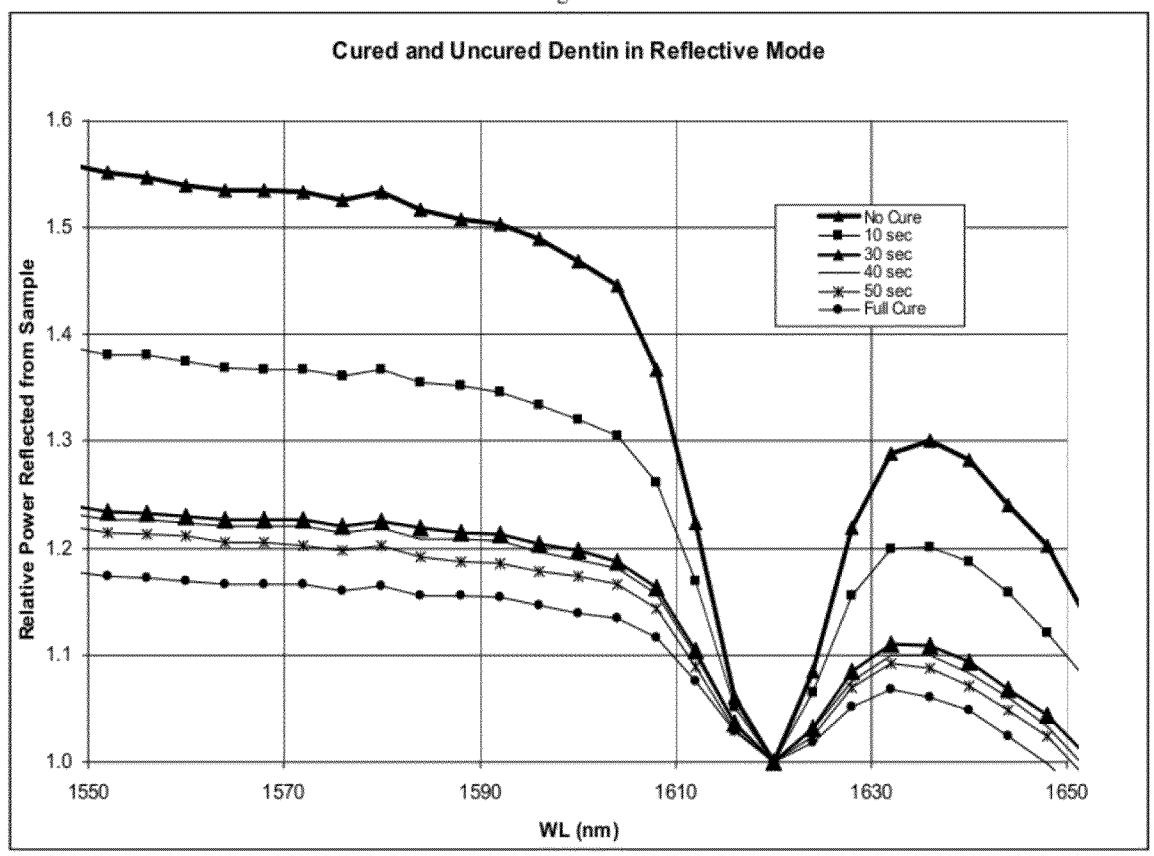
Figure 7C:
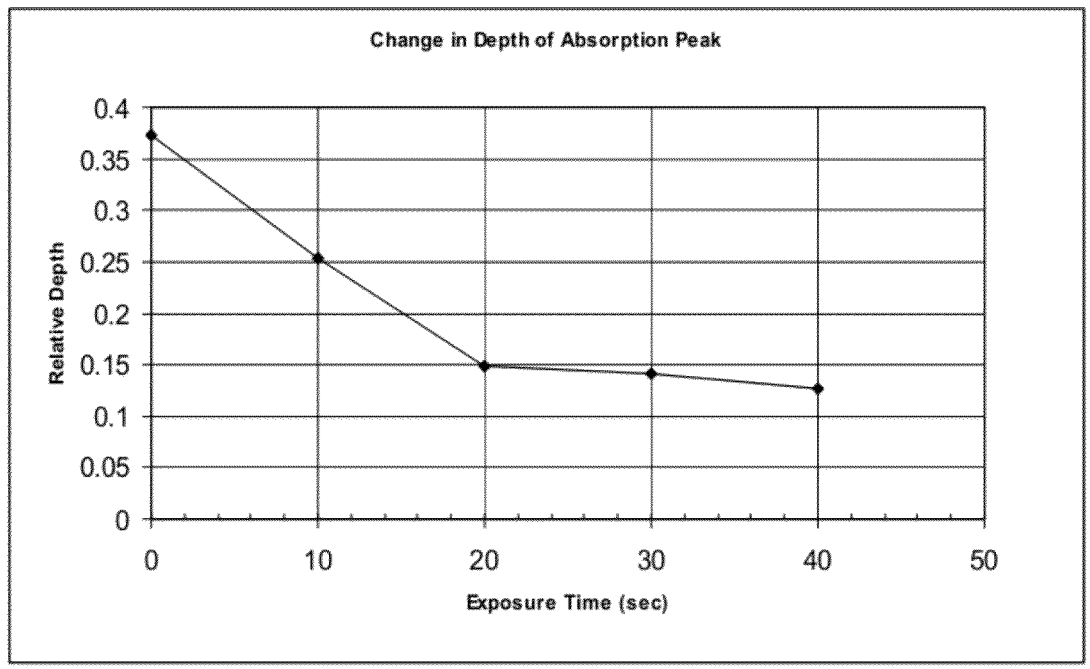
Figure 8A:
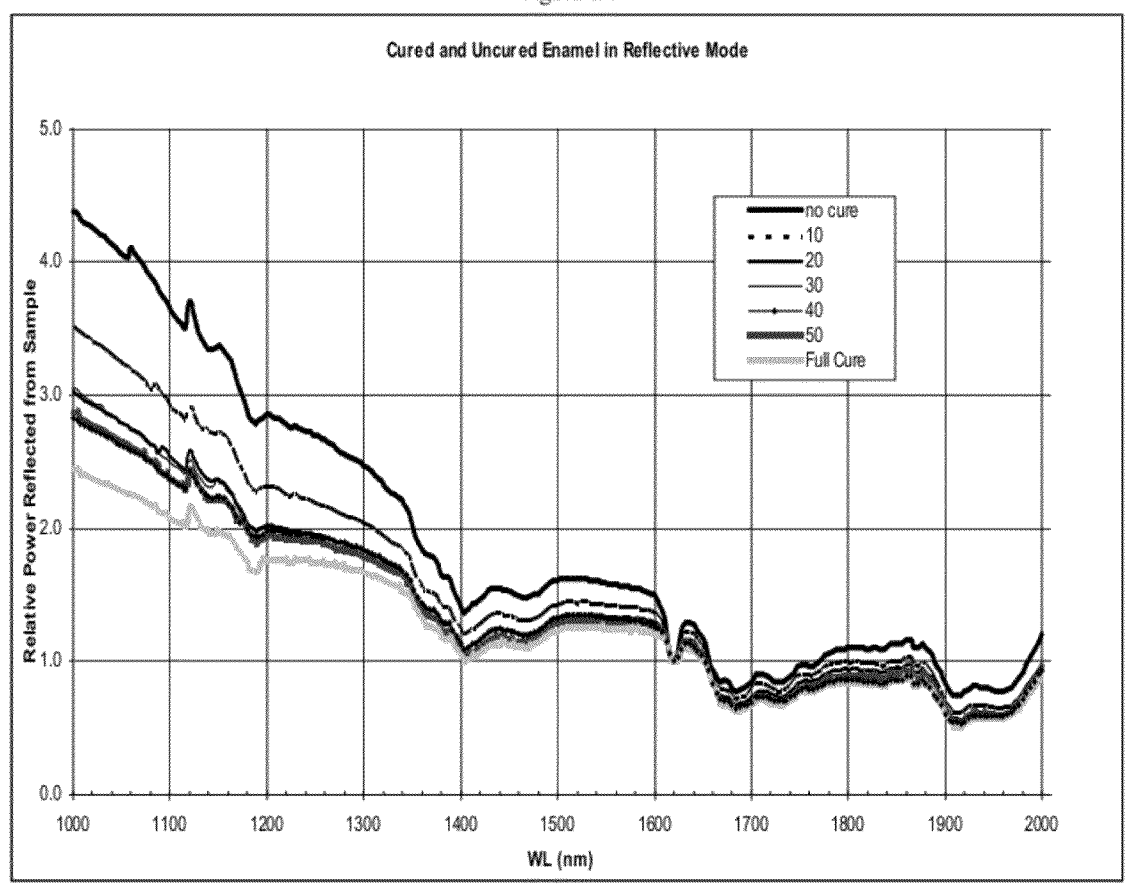
FIG. 8A, B, C are exemplary curves of enamel.
Figure 8B:
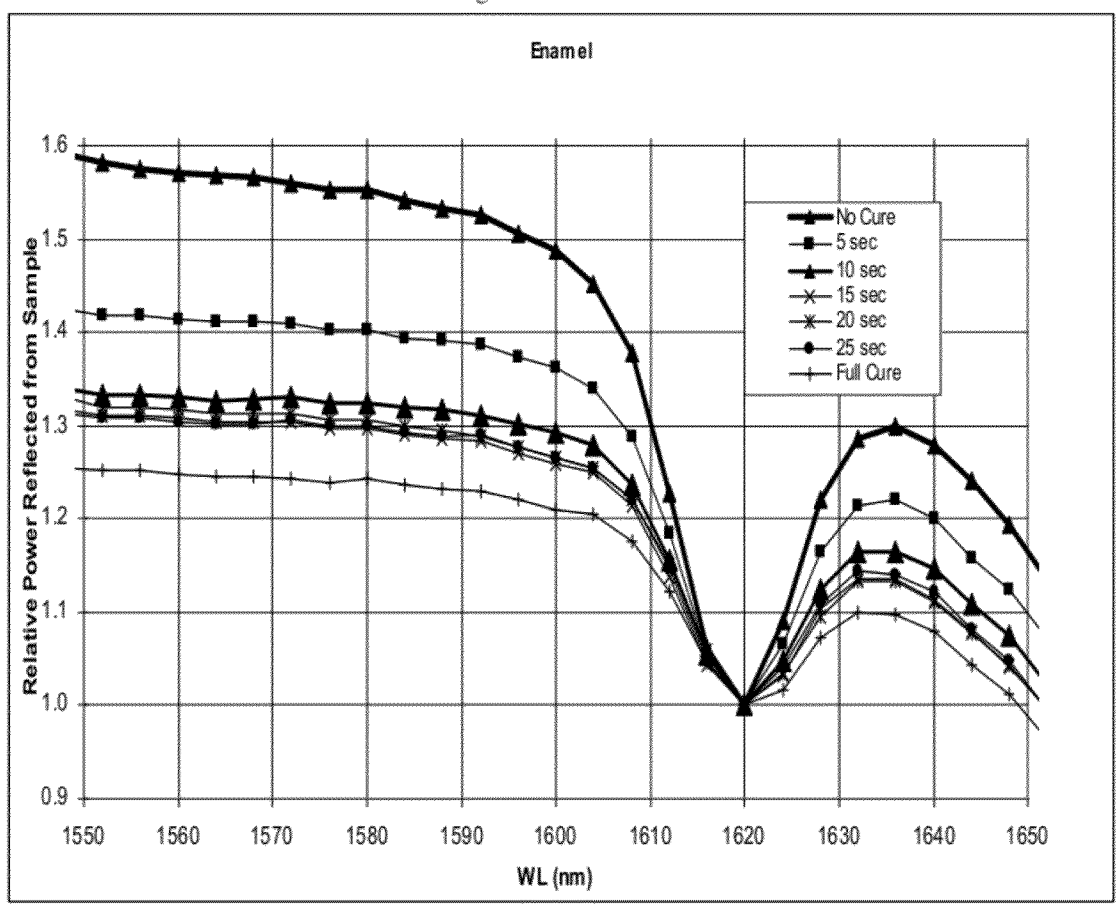
Figure 9A:
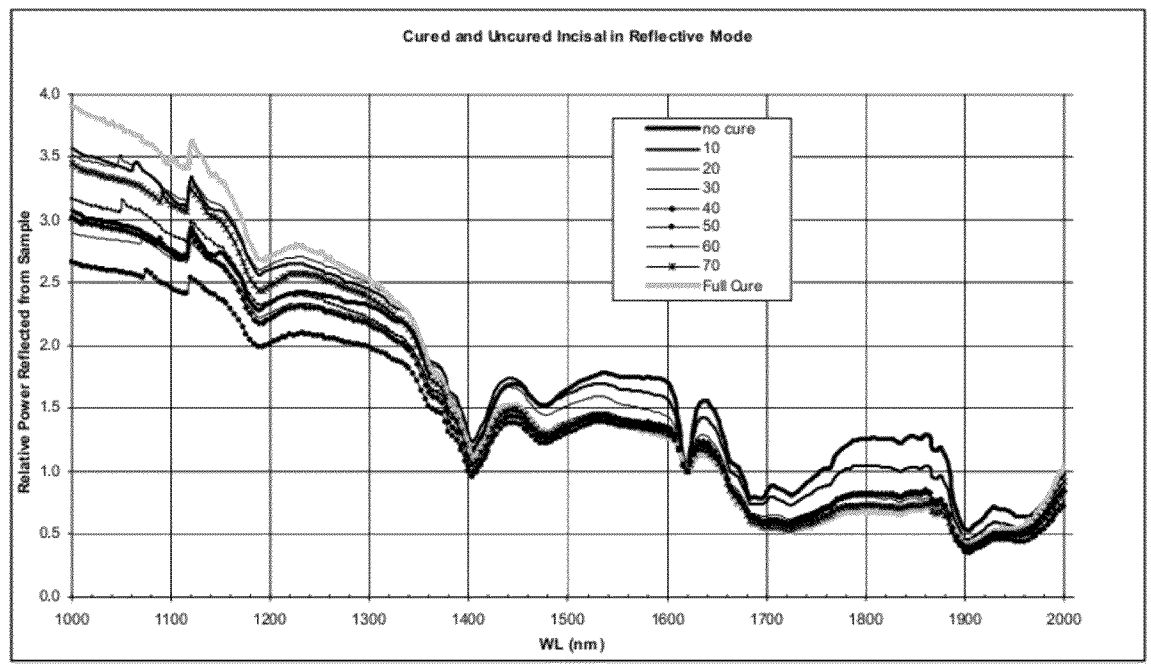
FIG. 9A, B, C are exemplary curves of Incisal.
Figure 9B:
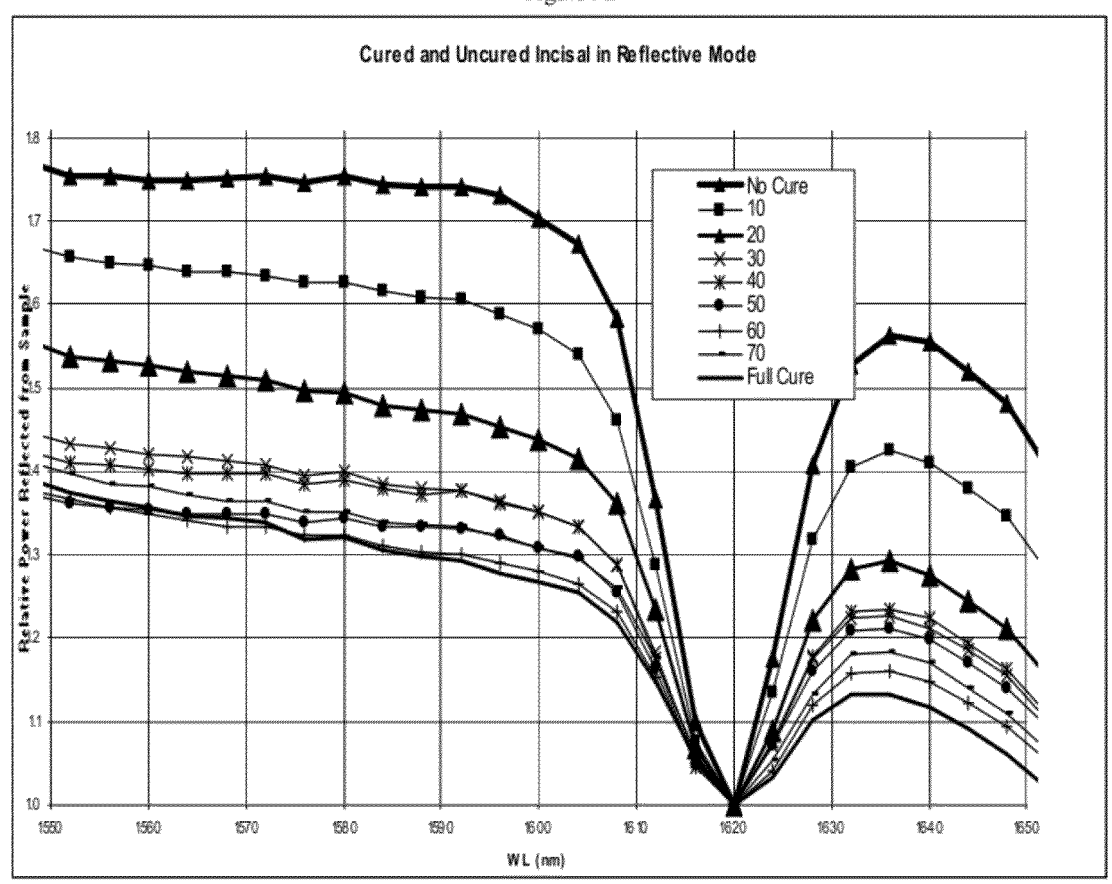
Figure 9C:
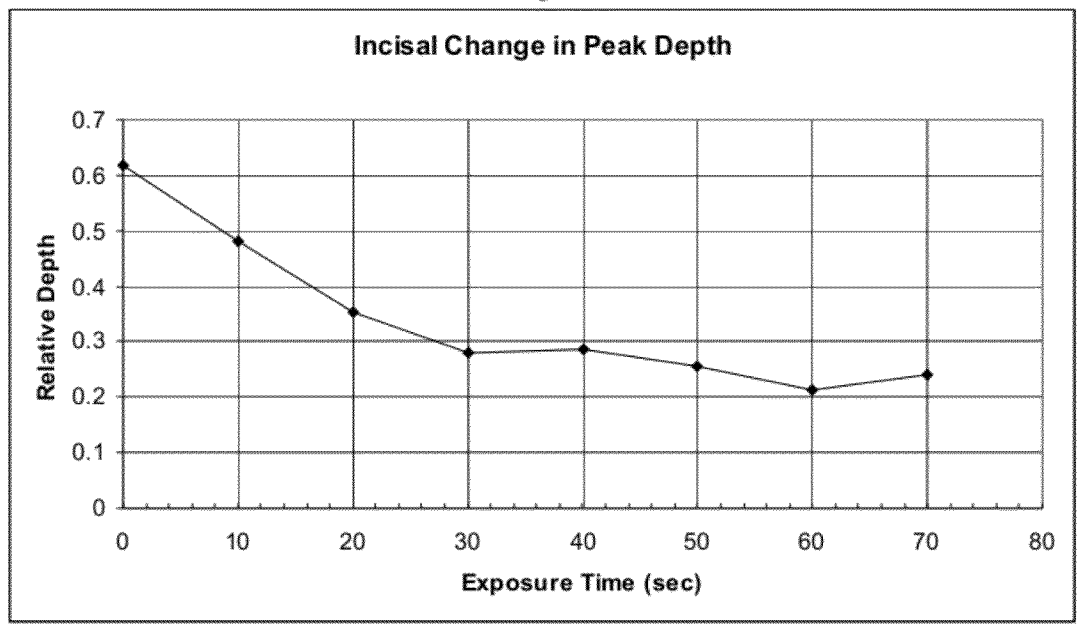
Figure 10:
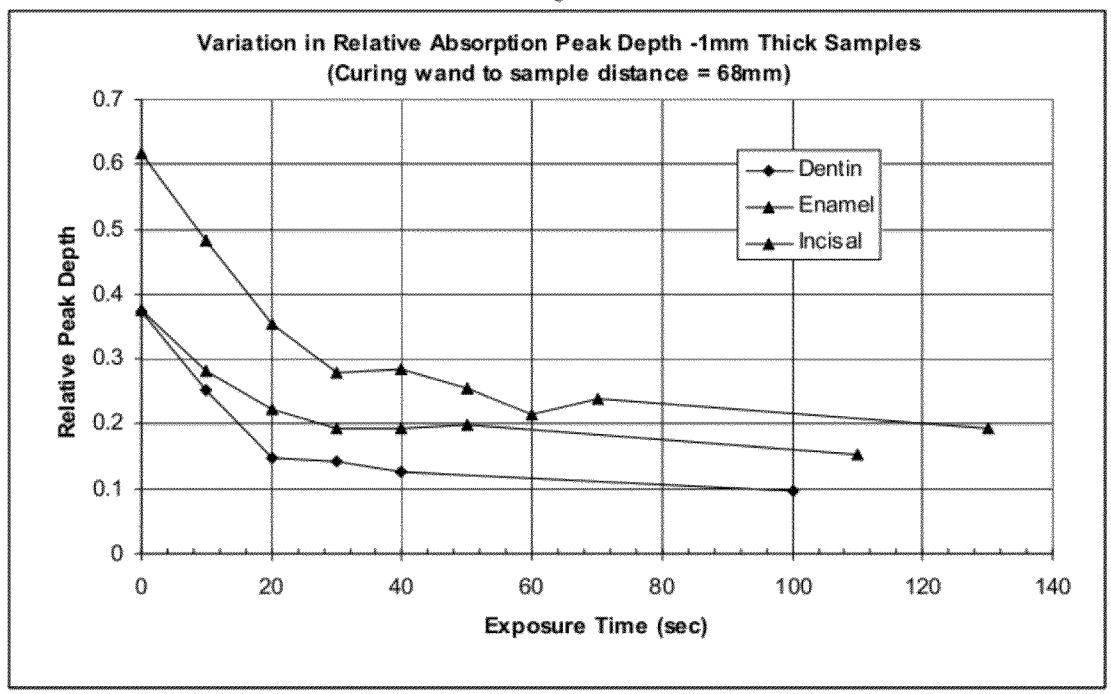
FIG. 10 are exemplary curves versus material.

FIG. 4 illustrates how a reflective mode system might be incorporated into a hand held device which is a key feature of the invention.

Projection and collector optiques are used to enhance the irradiance levels incident upon the sample as well the detectors. These optiques may be hollow reflective or solid refracting elements, utilizing spherical, parabolic, elliptical or other general aspheric surfaces. Optionally, surfaces may be reflectively coated or rely on total internal reflection (TIR) and/or Fresnel reflections.

An LED may act in either a passive or active mode regarding its interaction with a material under change in the context of its radiation being an initiator of a process, such as polymerization, or simply providing radiation to reflect off of the material.

In one embodiment of this invention photosensitive, adhesive materials are cured or polymerized by incident UV radiation interacting actively with a photo-initiator in an adhesive thereby initiating the curing process. An LED irradiates a sample at appropriate wavelengths; filtered detectors receive reflected radiation and one or more features illustrated in FIG. 2 are assessed to determine a level or degree of cure or other state change.

The following are exemplary applications of specific configurations of the instant invention; this list is not exhaustive; one knowledgeable in the art will be able to think of additional applications.

Measuring a degree of cure for UV or photo-curable acrylics and incorporating a shutoff system for the UV curing source based upon a spectral signature; customized for various applications such as dental.

Measuring the degree of cure for a acrylic or epoxy material whereby the beginning and ending material each has a specific spectral signature.

Identification of organic materials in delivery systems whereby the material has a spectral signature.

Identification of a material in a delivery system when a suitable fluorescent marker has been added for a measurable or specific spectral response.

Addition of an impurity or filler with a specific spectral signature, within a host material, suitable for identification and quality control. In some embodiments an added filler undergoes a spectral signature change during the process evolution of the host material when the host material has little or no or difficult spectral signature.

Identification of a cell material whereby a suitable marker protein is attached, as in abnormal cell structures.

Identification of a bacterial species whereby a suitable marker has been attached or in cases where the bacterial itself provides a suitable spectral signature.

Identification of a material structure that has undergone a structure change as a result of a process whereby the spectral signature has been changed by the process.

Identification of plasma constituents of a material with a suitable spectral signature, included within the plasma.

Identification of breath gas constituents, such as water and $CO_2$ content, as might be used in diagnosis for various diseases and abnormalities whereby the breath gas produces different constituents than the norm as might be found in diabetes, liver disease and various types of cancer and other abnormalities. In some embodiments an added gas undergoes a spectral signature change when exposed to a particular composition of gases related to a given health condition in the presence of a specific external radiation pattern.

Identification of fluid-based reactions in multi channel systems as might be used for blood and urine tests in multiple capillary diagnostic systems. Multiple spectral analysis modules can be combined for both up channel and down channel monitoring and identification. In some embodiments an added fluid undergoes a spectral signature change when exposed to a particular composition of fluids related to a given process in the presence of a specific external radiation pattern.

In one embodiment a spectral signature identification and/or monitoring system comprises means for real time data collection, enabling real time monitoring of a process thereby allowing for adjustments of, for example, source intensity, detector modulation, curing conditions, etc. to be made throughout the life of a process. In this manner a process may be sped up or slowed down by modulating the intensity of process driving factors, such as heat or radiation.

In one embodiment a spectral signature identification and/or monitoring system comprises both reflective and transmission modes simultaneously: The device is configured to operate in both the reflective and transmission modes simultaneously allowing for collection of forward pass absorption/transmission and back reflected/scattered characteristics coincidentally. In this manner more data is acquired enabling either a narrow bandwidth to be analyzed or more precise information obtained.

In one embodiment a spectral signature identification and/or monitoring system operates in both passive and active modes; a device is operated in passive, active or hybrid combination mode; passive mode referring to simply monitoring a process, active mode referring to supplying energy to enable or initiate a process. One embodiment is a hybrid epoxy curing system using a LED to actively cure a sample while passively monitoring the degree of cure with a different LED/detector combination. Feedback between the active LED and the passive LED/detector enables modulation of the process rate and end point.

In one embodiment a spectral signature identification and/or monitoring system uses multiple spectral signature characteristics, including, but not limited to, curve slope, intensity change, and absorption peak change, to characterize a process evolution: The use of combinations of various spectral signature characteristics enables extremely flexible test capabilities when the monitored changes in selected parameters are processed by signature identification algorithms; in some embodiments historical signature evolutions are compared to real time signature evolution as a technique for process evolution determination.

In one embodiment a spectral signature identification and/or monitoring system may utilize a feedback system to alter light source intensity and/or polarization/detector operation: A feedback system may be utilized to control characteristics of the LED output and those of the detector during the process and be utilized to control the nature of the process itself.

In one embodiment a spectral signature identification and/or monitoring system comprises a LED from Lumileds Lighting, a Luxeon™ Dental DS35; technical literature, included herein in its entirety by reference, is found at http://www.philipslumileds.com/pdfs/ds35.pdf, Aug. 31, 2009. Lumileds has a family of devices specifically for this market in the DS35 family. An exemplary detector is a Judson J23-18I-R500-1.9; an InGaAs detector; this particular device is intended for laboratory measurements. Other exemplary devices are available as plastic fiber communication devices from the telecom industry, which tend to be centered at the fiber transmission window around 1588 nm. An exemplary device for the region around 1620 nm are the Lasertechnik RLT1610-100MPG. In one embodiment a system uses a single emitter and a single detector for responses around 1600 nm. In one embodiment a system uses a silicon device for visible response; for near IR, detectors such as a GaSb go out to 3,000 nm to detect water vapor, CO and $CO_2$.

Figure 12:
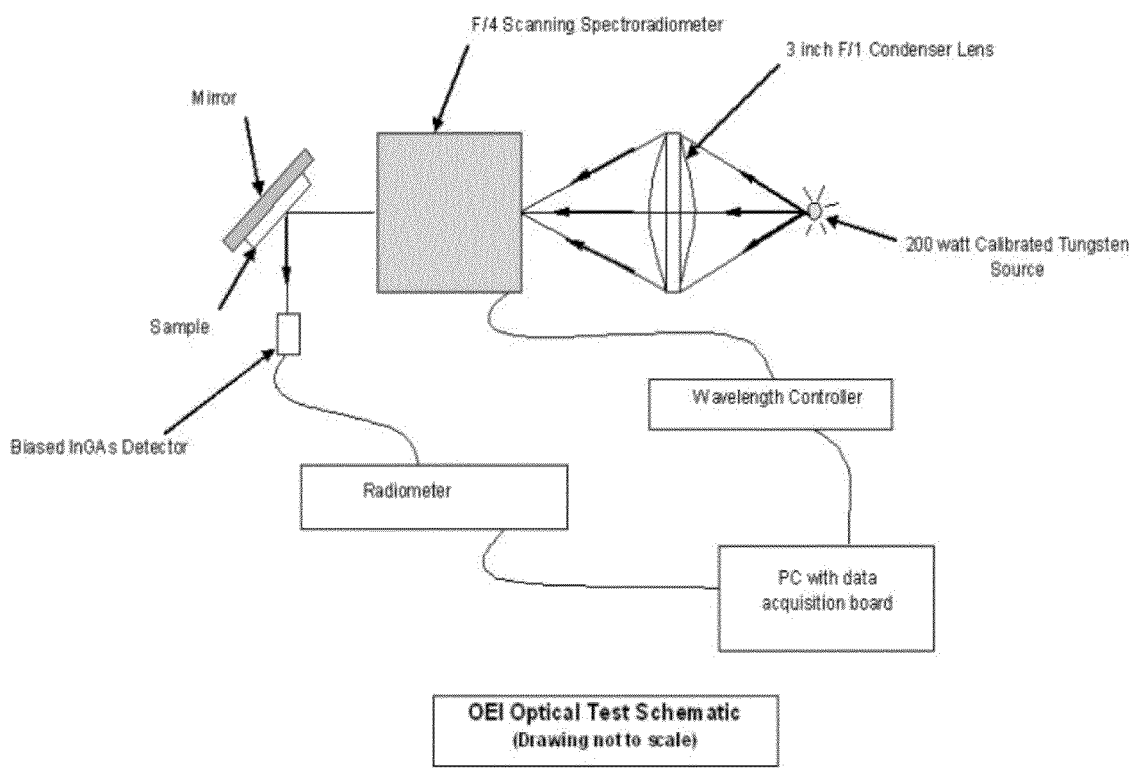
FIG. 12 is a schematic of the experimental apparatus.

A brief description of work characterizing several dental materials is presented to demonstrate various configurations of a spectral signature identification and/or monitoring system and methods for collecting data. Initial testing was performed on two samples of cured and one sample of uncured samples of Dentin A4, Enamel A2 and Incisal LT. The scan was from $0.38\mu$-$2.0\mu$. These wavelengths were chosen because of the availability of known emitters and detectors that could later be used for a spectroradiometric or a colorimetric identification process. FIG. 12 is a schematic of an experimental apparatus for collecting data.

At the same time, it was intended that a measurement technique be established with demonstrated repeatability and accuracy that could be used for future measurements. A transmissive configuration was used instead of a reflective configuration because of the ease of the optical set up. It is understood that in the actual application, that the detection system will need to be in a reflective configuration. The reflective configuration adds the additional complexity of looking at the Fresnel reflections of both the front and rear surface of the applied material against the tooth structure. The configuration used in this initial test was demonstrated to be repeatable and accurate.

Testing of the samples was performed with an OL740 spectroradiometer system using a 5 nm band pass. The samples were scanned from 380-1100 nm in 2 nm increments with the s/n 934 Si detector and a grating blazed at 500 nm. The scans from $1$-$2\mu$ were performed in increments of 2 nm with a 0.5 mm diameter InGaAs detector with a 0.1 volt reverse bias. Another grating blazed at $1.6\mu$ was used for dispersion. The light source was a 200 watt tungsten halogen lamp powered with the OL 65DS power supply. Due to expected low irradiance levels on the detector after transmission through the samples a f/1, 3 inch condenser lens was utilized to image the filament close to the entrance slit. Calibration files were created for both regions of the spectrum with the lens in place. The samples were positioned between the exit slit and the detector to minimize the irradiance incident upon them.

It should be noted that the data taken does not represent absolute values, but is normalized to the peak value for the composite curves and normalized to $1\mu$ for the final three curves, for the range of $1$-$2\mu$. Care was taken not to expose the uncured samples to UV or visible light for any periods of time more than necessary to complete the scan in an attempt to avoid the possibility of curing the sample during the measurement. Measurements were taken in the $1$-$2\mu$ range first.

The expected absorption at the $1.620\mu$ occurred with all uncured samples and almost disappeared for the cured samples. This appears to be repeatable and is an obvious point of interest for future study. Other areas of interest are: The significantly higher transmission of the uncured Dentin sample, and to a lesser extent for the Enamel, over the 1-2 u range; the differences in slope over the $1.1$-$1.2\mu$, $1.32$-$1.38\mu$ and $1.48$-$1.58\mu$ range for the Dentin sample; all uncured samples exhibited a higher peak at $1.705\mu$.

Using the method for transmissive measurements, measurements were made of both cured and uncured samples to determine both repeatability and any differences in curing techniques. FIGS. 3, and 7-10 show these curves and the conclusion can be reached that the significant features in specific spectral regions tend to match. The next procedure was to establish a reflective mode set up to measure standard samples and the necessary reflective surfaces.

Light from a calibrated (watts/$cm^2$/nm) 200 watt tungsten halogen is projected into the entrance slit of the spectrometer (representing a 5 nm band pass) via a 3 inch, F/1 condenser lens. The light is then dispersed into its constituent wavelengths by the internal rotating diffraction grating. As the grating rotates it directs the individual wavelengths to the exit slit which then strike the test sample at approximately 45 degrees. The sample is mounted to a stainless steel mirror to enhance throughput. The intensity of reflected light is then monitored with a biased (0.1 volt) InGaAs detector. Note that the reflected light is composed of four different elements:

Reflection from the front surface of the sample

Bulk scattering/reflection from the internal sample material

Reflection from the back surface of the sample

Reflection from the mirror which is then directed back through the sample.

The entire measurement process is controlled by a PC with data acquisition software and allows for data collection (watts/nm) from 350 nm to 2000 nm in variable increments and band pass. The samples were prepared using their annular stainless steel molds with microscope cover slides on either side to contain the sample material. All processing of the uncured samples was performed under controlled ambient light conditions. The data indicates that it is still possible to see the spectral characteristics of interest, namely the slopes of the curves and the absorption peak at 1620 nm. In general, the shape of the $1$-$2\mu$ curves was the same as we have seen in the transmissive mode.

In the next section, we did a time study of the spectral signature versus cure time, using the standard 1 mm sample disks in an effort to see how the characteristics of the curve were affected by an increasing level of cure. Samples were made using the standard method and disks and cured in 10 second intervals using a curing wand. As indicated, the focus of this analysis is on the reduction in depth of the 1620 nm absorption peak.

Except for the Incisal material, the depth of absorption seemed to reach an asymptotic value of between 0.1 and 0.2, after about 40 seconds, and for the Incisal material it was about 60 seconds. Note also that the distance of the curing wand was 68 mm. This was done in an attempt to provide a uniform field, but at this level the relative power at the surface of the sample was significantly reduced from the typical distance used in the application.

In the next series of measurements, the material thickness was increased to 2 mm by stacking two standard sample washers together. The curing process was similar but the curing wand was at a distance of 1 mm to increase the curing energy on the sample. Even though the actual curves for the timed interval spectral signature did not show a complete disappearance of the 1620 nm absorption peak, the curves of the relative depth did show a characteristic asymptotic decrease. The lack of complete disappearance may be due to the inhomogeneous cure in the unusually large and thick sample.

The conclusion of the data is that the ability to detect the decrease in absorption will allow a control signal to be generated that can be used to gate the driver for the cure LED, thereby automatically stopping the cure process. The necessary elements to do this would include a specific emitter/detector system and the associated optics, along with a signal processor that can be used to control the driver of the curing LED, providing the timed measurement interval as well as the final shut down. The system configuration allows for control of multiple emitters and multiple detectors, depending on the final measurement criteria. The driver may also include the curing emitter such that the processor can gate the cure emitter at an appropriate interval for the spectral signature measurement. Data collected and processed by the processor can be used for not only to determine the cure state, but can also be used for dynamic history feedback of the cure function and consequent correction of the process, and any other monitoring processes that might be required.

An optical packaging concept includes components of the existing cure wand as well as emitters and detectors and suitable optics, including a customized reflector and lensing, to direct and control the individual emitters and reflected signal.

The experimental data, note FIGS. 7-10, presented indicate that there are enough of spectral signature variations between cured and uncured material to develop an apparatus or means capable of discriminating between a cured and uncured state and in some embodiments determine a degree of cure. For the materials examined one spectral region of interest is the 1,620 nm absorption peak. Other areas for consideration depend on the characteristics of the material and other property identification tasks that might be assigned to the optical system, such as material identification. Another issue to be determined by experimentation is the correlation between an actual chemical, and/or mechanical, degree of cure versus a perceived "optical degree" of cure so that a desired cure point can be defined in terms of an "optical cure point", suitable for use as criteria by a device with optical sensing.

Using the previously defined reflective mode configuration, 2 mm samples of Dentin A4 were subjected to a timed UV cure in increments of 10 seconds, with the curing wand at a fixed spacing of 68 mm. As before, this was done to assure a uniform cure across the diameter of the sample and also to be able to compare to previous data.

Figure 11:
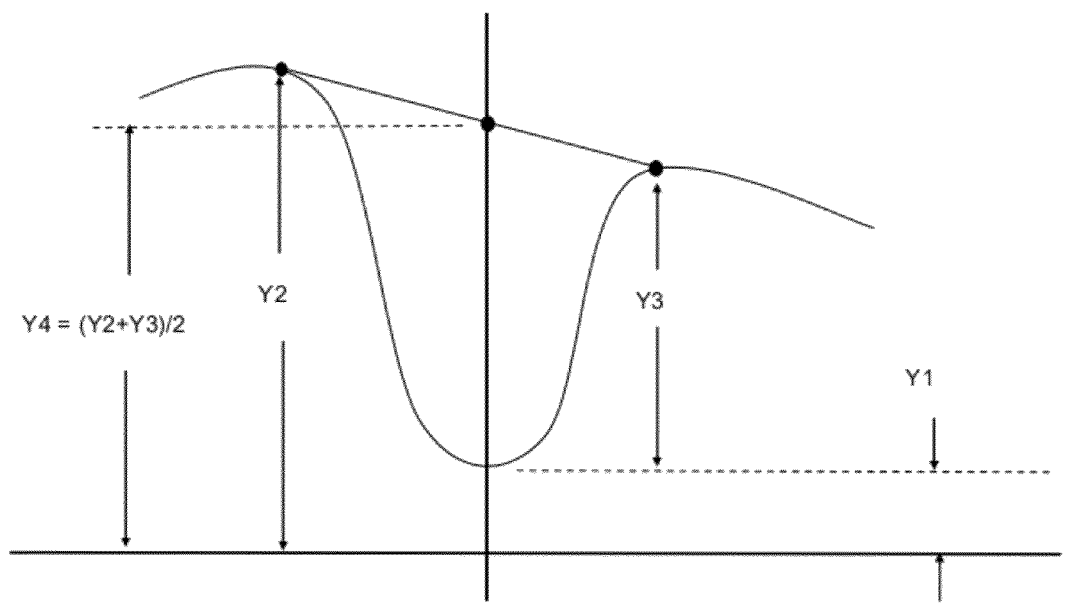
FIG. 11 is a description of the adsorption depth calculation.

FIG. 11 defines the formula for the definition of "depth of cure" as used. In the case of these results, both sides show the same type of asymptotic cure function. Interestingly it appears that the "back" or $2^{nd}$ side exhibited a higher level of cure than the "front" or $1^{st}$ side. As noted later, this may be because of the minor mounting scheme during the cure.

The next step of the experiment was to determine the effect of the mirror on the reflected energy, thereby providing an indication of how much energy was being transmitted through the back surface and reflected back into the sample. This was done by providing a fixture such that the mirror could be removed after an initial measurement without disturbing the location of the sample in the test setup, such that the optical energy was incident on the sample in the same location. The results of this test are that approximately 40% of the energy is coming back through the sample. Considering that some of the remaining 60% of the energy is reflected off of the back surface and that another percentage is the result of bulk scattering throughout the sample, we might conclude that the resultant energy represents close to a 50/50 distribution between the front surface and back surface, including bulk scattering; therefore the detector detecting all the energy from the sample is also seeing a reasonable distribution of cure throughout the bulk of the sample. The results give a reasonable indication of cure at the bottom of the 2 mm depth. Herein we disclose that there is a correlation between a laboratory cure process and Rockwell hardness data so that a definitive relationship exists to enable data from the detector in the system processor to be transformed into meaningful signals indicating degree of cure.

In some embodiments a device for monitoring a chemical reaction comprises a means for emitting radiation, a means for currently acquiring a spectral signature response in time of the chemical reaction, and a processor comprising means for storing a plurality of spectral signature responses and means for comparing currently acquired spectral signature responses and stored reference spectral signature responses; wherein reference spectral signature responses are a sequence of spectral signatures in time of the chemical reaction acquired previously such that at predetermined intervals the currently acquired spectral signature response of the chemical reaction is compared to a reference spectral signature response and a signal is communicated or not based upon the comparing; optionally, the device may be held in a hand; optionally, the device comprises at least a first and second means for emitting radiation wherein at least the first means is emitting at less than 600 nm; optionally the intensity of said first means for emitting radiation is modulated based on said comparing; optionally, the means for emitting comprises a LED or a solid state laser emitting at a predetermined wavelength, $\lambda$, ±3 nm; optionally, the degree of completion of said chemical reaction is determined based upon the rate of change of said acquired spectral signature response; optionally, the degree of completion of said chemical reaction is determined based upon a decrease in absolute magnitude of said acquired spectral signature response or a change in slope; optionally, the degree of completion of said chemical reaction is determined based upon a change in slope of said acquired spectral signature response; optionally, the degree of completion of said chemical reaction is determined based upon a change in an adsorption band of said acquired spectral signature response; optionally, the degree of completion of said chemical reaction is determined based upon a change in one or more of the following parameters of said acquired spectral signature response chosen from a group consisting of polarization, bidirectional reflectance distribution function (BRDF), bidirectional transmission distribution function (BTDF), Raman scattering, Rayleigh scattering and Fourier transforms; optionally, a means for emitting radiation comprises a projection optique comprising at least one element or surface chosen from a group consisting of hollow reflective elements, solid refracting elements, spherical surface, parabolic surface, elliptical surface and a general aspheric surface; optionally, a means for currently acquiring a spectral signature response comprises a collector optique comprising at least one element or surface chosen from a group consisting of hollow reflective elements, solid refracting elements, spherical surface, parabolic surface, elliptical surface and a general aspheric surface.

In some embodiments a device for determining the composition of a fluid comprises a means for emitting radiation, a means for currently acquiring a spectral signature response in time of the emitted radiation after contact with the fluid, and a processor comprising means for storing a plurality of spectral signature responses and means for comparing currently acquired spectral signature responses and stored reference spectral signature responses; wherein reference spectral signature responses are a sequence of spectral signatures in time acquired previously such that at predetermined intervals the currently acquired spectral signature response of the fluid is compared to a reference spectral signature response and a signal is communicated or not based upon the comparing; optionally, the device may be held in a hand; optionally, the device further comprises at least a first and second means for emitting radiation wherein at least the first means is emitting at less than 600 nm; optionally, the intensity of said means for emitting radiation is modulated based on said comparing; optionally, the means for emitting comprises a LED or a solid state laser emitting at a predetermined wavelength, $\lambda$, ±3 nm.

In some embodiments a device for determining the composition of a material comprises a means for emitting radiation at two predetermined wavelengths, $\lambda_1$±3 nm and $\lambda_2$±3 nm, a means for currently acquiring a spectral signature response in time of the emitted radiation after contact with the material, and a processor comprising means for storing a plurality of spectral signature responses and means for comparing currently acquired spectral signature responses and stored reference spectral signature responses; wherein reference spectral signature responses are a sequence of spectral signatures in time acquired previously such that at predetermined intervals the currently acquired spectral signature response of the material is compared to a reference spectral signature response and a signal is communicated or not based upon the comparing; optionally, the device may be held in a hand; optionally, $\lambda_1$±3 nm is less than 600 nm; optionally, the intensities of $\lambda_1$ and $\lambda_2$ are modulated based upon said comparing; optionally, the means for emitting comprises a LED or a solid state laser; optionally, the degree of completion of said chemical reaction is determined based upon the rate of change of said acquired spectral signature response; optionally, the degree of completion of said chemical reaction is determined based upon a decrease in absolute magnitude of said acquired spectral signature response or a change in slope; optionally, the degree of completion of said chemical reaction is determined based upon a change in slope of said acquired spectral signature response; optionally, the degree of completion of said chemical reaction is determined based upon a change in an adsorption band of said acquired spectral signature response; optionally, the degree of completion of said chemical reaction is determined based upon a change in one or more of the following parameters of said acquired spectral signature response chosen from a group consisting of polarization, bidirectional reflectance distribution function (BRDF), bidirectional transmission distribution function (BTDF), Raman scattering, Rayleigh scattering and Fourier transforms; optionally, the means for emitting radiation comprises a projection optique comprising at least one element or surface chosen from a group consisting of hollow reflective elements, solid refracting elements, spherical surface, parabolic surface, elliptical surface and a general aspheric surface; optionally, the means for currently acquiring a spectral signature response comprises a collector optique comprising at least one element or surface chosen from a group consisting of hollow reflective elements, solid refracting elements, spherical surface, parabolic surface, elliptical surface and a general aspheric surface.

All patents, patent applications, and other documents referenced herein are incorporated by reference in their entirety for all purposes, unless otherwise indicated.

Foregoing described embodiments of the invention are provided as illustrations and descriptions. They are not intended to limit the invention to precise form described. In particular, it is contemplated that functional implementation of invention described herein may be implemented equivalently. Alternative construction techniques and processes are apparent to one knowledgeable with integrated circuit, LED, lighting and/or MEMS technologies. Other variations and embodiments are possible in light of above teachings, and it is thus intended that the scope of invention not be limited by this Detailed Description, but rather by Claims following.

We claim:

1. A device for monitoring a chemical reaction comprising:
   a means for emitting radiation;
   a means for currently acquiring a spectral signature response in time of the chemical reaction; and
   a processor comprising means for storing a plurality of spectral signature responses and means for comparing currently acquired spectral signature responses and stored reference spectral signature responses; wherein reference spectral signature responses are a sequence of spectral signatures in time of the chemical reaction acquired previously such that at predetermined intervals the currently acquired spectral signature response of the chemical reaction is compared to a reference spectral signature response and a signal is communicated or not based upon the comparing.

2. The device of claim 1 wherein the device is held in a hand.

3. The device of claim 1 wherein the device further comprises at least a first and second means for emitting radiation wherein at least the first means is emitting at less than 600 nm.

4. The device of claim 3 wherein the intensity of said first means for emitting radiation is modulated based on said comparing.

5. The device of claim 1 wherein the means for emitting comprises a LED or a solid state laser emitting at a predetermined wavelength, $\lambda$, ±3 nm.

6. The device of claim 1 wherein the degree of completion of said chemical reaction is determined based upon the rate of change of said acquired spectral signature response.

7. The device of claim 1 wherein the degree of completion of said chemical reaction is determined based upon a decrease in absolute magnitude of said acquired spectral signature response or a change in slope.

8. The device of claim 1 wherein the degree of completion of said chemical reaction is determined based upon a change in slope of said acquired spectral signature response.

9. The device of claim 1 wherein the degree of completion of said chemical reaction is determined based upon a change in an adsorption band of said acquired spectral signature response.

10. The device of claim 1 wherein the degree of completion of said chemical reaction is determined based upon a change in one or more of the following parameters of said acquired spectral signature response chosen from a group consisting of polarization, bidirectional reflectance distribution function (BRDF), bidirectional transmission distribution function (BTDF), Raman scattering, Rayleigh scattering and Fourier transforms.

11. The device of claim 1 wherein said means for emitting radiation comprises a projection optique comprising at least one element or surface chosen from a group consisting of hollow reflective elements, solid refracting elements, spherical surface, parabolic surface, elliptical surface and a general aspheric surface.

12. The device of claim 1 wherein said means for currently acquiring a spectral signature response comprises a collector optique comprising at least one element or surface chosen from a group consisting of hollow reflective elements, solid refracting elements, spherical surface, parabolic surface, elliptical surface and a general aspheric surface.

13. A device for determining the composition of a fluid comprising;
   a means for emitting radiation;
   a means for currently acquiring a spectral signature response in time of the emitted radiation after contact with the fluid; and
   a processor comprising means for storing a plurality of spectral signature responses and means for comparing currently acquired spectral signature responses and stored reference spectral signature responses; wherein reference spectral signature responses are a sequence of spectral signatures in time acquired previously such that at predetermined intervals the currently acquired spectral signature response of the fluid is compared to a reference spectral signature response and a signal is communicated or not based upon the comparing.

14. The device of claim 13 wherein the device is held in a hand.

15. The device of claim 13 wherein the device further comprises at least a first and second means for emitting radiation wherein at least the first means is emitting at less than 600 nm.

16. The device of claim 13 wherein the intensity of said means for emitting radiation is modulated based on said comparing.

17. The device of claim 13 wherein the means for emitting comprises a LED or a solid state laser emitting at a predetermined wavelength, $\lambda$, $\pm 3$ nm.

18. A device for determining the composition of a material comprising;
   a means for emitting radiation at two predetermined wavelengths, $\lambda_1 \pm 3$ nm and $\lambda_2 \pm 3$ nm;
   a means for currently acquiring a spectral signature response in time of the emitted radiation after contact with the material; and
   a processor comprising means for storing a plurality of spectral signature responses and means for comparing currently acquired spectral signature responses and stored reference spectral signature responses; wherein reference spectral signature responses are a sequence of spectral signatures in time acquired previously such that at predetermined intervals the currently acquired spectral signature response of the material is compared to a reference spectral signature response and a signal is communicated or not based upon the comparing.

19. The device of claim 18 wherein the device is held in a hand.

20. The device of claim 18 wherein $\lambda_1 \pm 3$ nm is less than 600 nm.

21. The device of claim 18 wherein the intensities of $\lambda_1$ and $\lambda_2$ are modulated based upon said comparing.

22. The device of claim 18 wherein the means for emitting comprises a LED or a solid state laser.

23. The device of claim 18 wherein the degree of completion of said chemical reaction is determined based upon the rate of change of said acquired spectral signature response.

24. The device of claim 18 wherein the degree of completion of said chemical reaction is determined based upon a decrease in absolute magnitude of said acquired spectral signature response or a change in slope.

25. The device of claim 18 wherein the degree of completion of said chemical reaction is determined based upon a change in slope of said acquired spectral signature response.

26. The device of claim 18 wherein the degree of completion of said chemical reaction is determined based upon a change in an adsorption band of said acquired spectral signature response.

27. The device of claim 18 wherein the degree of completion of said chemical reaction is determined based upon a change in one or more of the following parameters of said acquired spectral signature response chosen from a group consisting of polarization, bidirectional reflectance distribution function (BRDF), bidirectional transmission distribution function (BTDF), Raman scattering, Rayleigh scattering and Fourier transforms.

28. The device of claim 18 wherein said means for emitting radiation comprises a projection optique comprising at least one element or surface chosen from a group consisting of hollow reflective elements, solid refracting elements, spherical surface, parabolic surface, elliptical surface and a general aspheric surface.

29. The device of claim 18 wherein said means for currently acquiring a spectral signature response comprises a collector optique comprising at least one element or surface chosen from a group consisting of hollow reflective elements, solid refracting elements, spherical surface, parabolic surface, elliptical surface and a general aspheric surface.

* * * * *